US011305030B2

(12) United States Patent
Drmanovic

(10) Patent No.: US 11,305,030 B2
(45) Date of Patent: Apr. 19, 2022

(54) DISINFECTING CAP WITH TOP OPENING

(71) Applicant: DRMA GROUP INTERNATIONAL LLC, Palm City, FL (US)

(72) Inventor: Zoran Drmanovic, Palm City, FL (US)

(73) Assignee: DRMA Group International LLC, Palm City, FL (US)

(*) Notice: Subject to any disclaimer, the term of this patent is extended or adjusted under 35 U.S.C. 154(b) by 17 days.

(21) Appl. No.: 16/288,572

(22) Filed: Feb. 28, 2019

(65) Prior Publication Data

US 2020/0276346 A1 Sep. 3, 2020

(51) Int. Cl.
*A61L 2/26* (2006.01)
*A61M 39/02* (2006.01)
*A61L 2/16* (2006.01)

(52) U.S. Cl.
CPC .......... *A61L 2/26* (2013.01); *A61L 2/16* (2013.01); *A61M 39/02* (2013.01); *A61L 2202/121* (2013.01); *A61L 2202/122* (2013.01); *A61L 2202/123* (2013.01); *A61L 2202/24* (2013.01); *A61M 2039/0205* (2013.01); *A61M 2039/0285* (2013.01)

(58) Field of Classification Search
CPC ........ A61L 2/26; A61L 2/16; A61L 2202/123; A61L 2202/122; A61L 2202/121; A61L 2202/24; A61L 2/18; A61L 2202/23; A61M 39/02; A61M 2039/0205; A61M 2039/0285
See application file for complete search history.

(56) References Cited

U.S. PATENT DOCUMENTS

| 4,043,333 A * | 8/1977 | Munsch ............... A61M 39/04 604/86 |
| 4,405,312 A * | 9/1983 | Gross ...................... A61L 2/18 604/29 |
| 4,753,358 A * | 6/1988 | Virca .................. B01L 3/50825 215/230 |
| 5,885,249 A * | 3/1999 | Irisawa ............... A61M 5/3216 604/111 |
| 6,916,051 B2 * | 7/2005 | Fisher ............... A61M 39/1011 285/371 |
| 7,682,561 B2 * | 3/2010 | Davis ...................... A61L 2/18 422/28 |

(Continued)

*Primary Examiner* — Regina M Yoo
(74) *Attorney, Agent, or Firm* — Dmitry Zuev, Esq.

(57) ABSTRACT

A device for disinfecting a portion of a medical implement includes two disinfecting chambers, wherein each disinfecting chamber includes a wall forming a medial and bottom openings, which are in communication with each other, wherein one disinfecting chamber is opposed to the other. Each disinfecting chamber houses a disinfecting member that is exposed through the medial opening to come into communication with a medical implement when the disinfecting chambers are closed. The device further includes a resilient member connected to the two disinfecting chambers, which biases the disinfecting chambers together to a closed position and permits displacement of the disinfecting chambers to an open position, such that the medial opening of one disinfecting chamber communicates with the medial opening of the other disinfecting chamber and the bottom opening of one chamber communicates with the bottom opening of the other chamber when in the closed position.

17 Claims, 4 Drawing Sheets

(56) References Cited

U.S. PATENT DOCUMENTS

| | | | | |
|---|---|---|---|---|
| 7,931,877 | B2* | 4/2011 | Steffens | A61L 2/18 |
| | | | | 422/292 |
| 10,391,294 | B2* | 8/2019 | Drmanovic | A61M 39/165 |
| 10,576,259 | B2* | 3/2020 | Stafford | A61M 5/1418 |
| 2009/0175759 | A1* | 7/2009 | Davis | A61L 2/18 |
| | | | | 422/28 |
| 2010/0292673 | A1* | 11/2010 | Korogi | A61M 39/20 |
| | | | | 604/533 |
| 2012/0016318 | A1* | 1/2012 | Hoang | A61M 39/16 |
| | | | | 604/288.01 |
| 2013/0171030 | A1* | 7/2013 | Ferlic | A61L 2/18 |
| | | | | 422/119 |
| 2015/0017062 | A1* | 1/2015 | Dam | A61L 2/18 |
| | | | | 422/28 |
| 2015/0374969 | A1* | 12/2015 | Mobassery | A61M 25/00 |
| | | | | 604/500 |
| 2019/0009074 | A1* | 1/2019 | Drmanovic | A61L 2/18 |

* cited by examiner

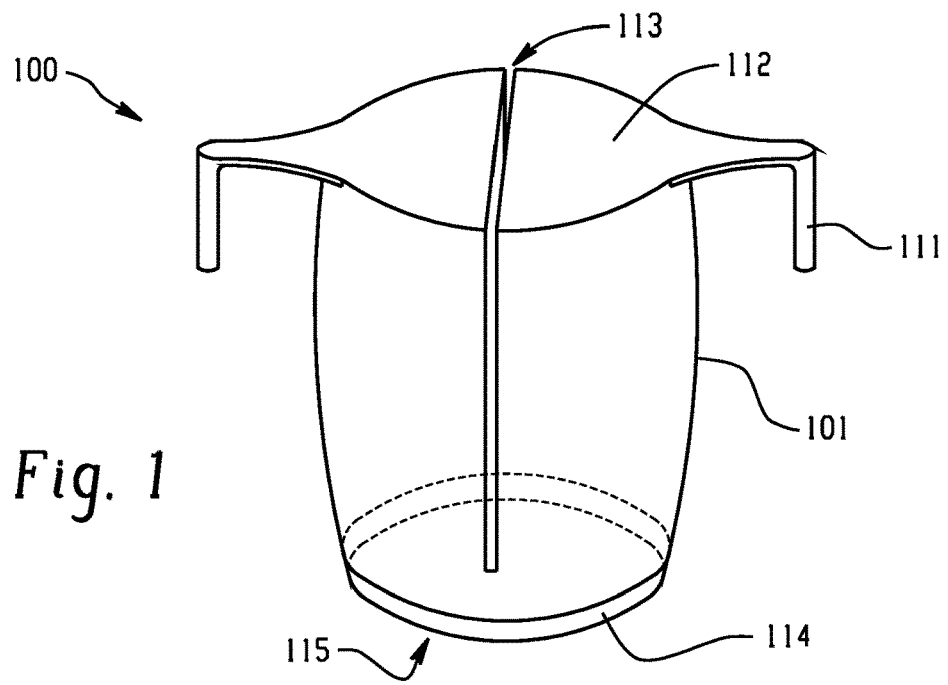
Fig. 1
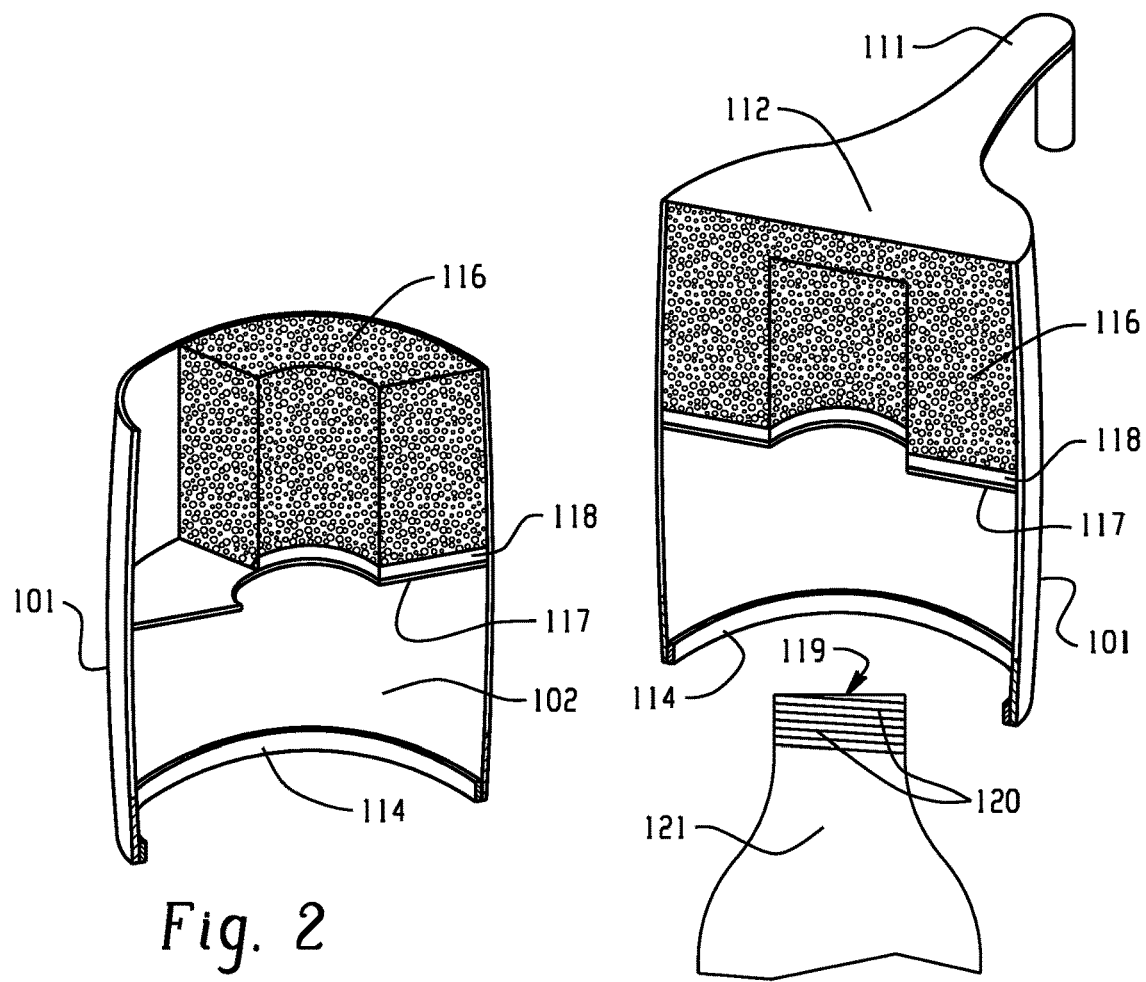
Fig. 2
Fig. 3

DISINFECTING CAP WITH TOP OPENING

BACKGROUND

The present invention generally relates to a device having disinfecting properties, and more specifically, to a capping device for disinfecting a hub or injection port.

Presence of intravenous catheters is the major risk factor for the development of bloodstream infections. These catheters can be either central or peripheral. Needleless hub connectors are ordinarily used as an injection port on the catheters. A typical connector includes a female luer lock, and usually, a syringe with a male luer lock is used to inject fluids or medications.

Needleless hub connector contamination is a major risk factor for bloodstream infection. Scrubbing the female luer lock with alcohol for 10-60 seconds is recommended before each use, but this procedure is often omitted by medical professionals. Studies have shown better results in reducing infection with different types of alcohol impregnated protectors, such as Swab Cap® by ICU Medical or Curos® by 3M. However, because the protector constitutes a separate entity, only the most diligent medical professionals would utilize them after every step. In addition, the cap does not assure mandatory compliance. Caps do not always engage the threads on the hub, and the threads can serve as a source of infection, especially, if a dirty or bloody male luer from the syringe is used to engage the hub. Also, because of their small size, the caps are easily lost or contaminated after use if they are placed on a contaminated surface. Medical provider might forget to put it back, place dirty cap back onto the hub or need to use a new clean cap. Those caps also require two hands to attach or detach the cap from the hub while the present invention requires provider to use only one hand to hold and open the top of the invention while the other one is used to connect syringe and inject.

Attempts have been made to cover the hub in order to keep it disinfected. However, these efforts either failed to cover the hub completely by shielding only the top membrane, or were too difficult to remove when the port needed to be injected quickly and conveniently.

Thus, there remains a need for a convenient and reliable disinfecting device that would stay at the top of needleless hub all the time, would guarantee 100% compliance of medical professionals with antiseptic techniques and at the same time be very easy to open in order to connect with a syringe.

SUMMARY

An embodiment provides a device for disinfecting a portion of a medical implement, comprising:
 two disinfecting chambers,
  wherein each disinfecting chamber includes a wall forming a medial opening and a bottom opening, wherein the medial opening and the bottom opening are in communication with each other, and wherein one disinfecting chamber is opposed to the other, and
  wherein each disinfecting chamber houses a disinfecting member that is exposed through the medial opening to come into communication with a medical implement when the disinfecting chambers are closed; and
 a resilient member connected to the two disinfecting chambers,
  wherein the resilient member biases the disinfecting chambers together to a closed position and permits displacement of the disinfecting chambers to an open position, such that the medial opening of one disinfecting chamber communicates with the medial opening of the other disinfecting chamber and the bottom opening of one chamber communicates with the bottom opening of the other chamber when in the closed position,
  wherein the medial and bottom openings of each disinfecting chamber are substantially configured to receive and be biased against a medical implement.

Each disinfecting chamber further include a sealing member separating the medial and bottom openings.

The sealing member may include an elevated central rim.

The disinfecting member may be disposed over the entire surface of a chamber formed by an internal surface of the wall and the medial opening.

The disinfecting chamber may further include a hollow disposed between the disinfecting member and the medial opening, wherein the shape of the hollow may substantially match the shape of a portion of the medical implement to be disinfected.

The disinfecting chambers may displace relative to each other so as to create a cavity between them.

Each disinfecting chamber may further include a handle disposed on an external surface of the wall, wherein the disinfecting chambers may displace by application of a force to the handle.

Alternatively, the disinfecting chambers displace by application of a force directly to an external surface of the wall of the disinfecting chamber.

The disinfecting members may directly contact each other in the closed position.

The disinfecting members may be impregnated with the disinfecting agent.

Another embodiment provides a device for disinfecting a portion of a medical implement, including:
 two disinfecting chambers,
  wherein each disinfecting chamber includes a wall forming a medial opening and a bottom opening, wherein the medial opening and the bottom opening are in communication with each other, and wherein one disinfecting chamber is opposed to the other, and
  wherein each disinfecting chamber houses a disinfecting member that is exposed through the medial opening to come into communication with a medical implement when the disinfecting chambers are closed;
 a resilient member connected to the two disinfecting chambers,
  wherein the resilient member biases the disinfecting chambers together to a closed position and permits displacement of the disinfecting chambers to an open position, such that the medial opening of one disinfecting chamber communicates with the medial opening of the other disinfecting chamber and the bottom opening of one chamber communicates with the bottom opening of the other chamber when in the closed position; and
 a medical implement protruded through a bottom opening of each disinfecting chamber with a portion to be disinfected exposed inside a chamber formed by the wall and the medial opening.

When the disinfecting members are in contact with the portion to be disinfected, the disinfecting members release the disinfecting agent onto the portion to be disinfected.

The resilient member may be permanently affixed to the medical implement so as to form a single entity.

Alternatively, the resilient member and the medical implement may not permanently affixed.

The portion to be disinfected may be a needleless hub or an injection port.

The portion to be disinfected may include a female luer fitting and an injection membrane.

A combined internal surface of the wall of both disinfecting chambers in the closed position may fully encircle the portion of the medical implement to be disinfected.

The portion to be disinfected in the open position may be completely uncovered.

Yet another embodiment provides a method for automatically disinfecting a portion of a medical implement, including:

two disinfecting chambers,
wherein each disinfecting chamber includes a wall forming a medial opening and a bottom opening, wherein the medial opening and the bottom opening are in communication with each other, and wherein one disinfecting chamber is opposed to the other, and
wherein each disinfecting chamber houses a disinfecting member that is exposed through the medial opening to come into communication with a medical implement when the disinfecting chambers are closed;
a resilient member connected to the two disinfecting chambers,
wherein the resilient member biases the disinfecting chambers together to a closed position and permits displacement of the disinfecting chambers to an open position, such that the medial opening of one disinfecting chamber communicates with the medial opening of the other disinfecting chamber and the bottom opening of one chamber communicates with the bottom opening of the other chamber when in the closed position; and
a medical implement protruded through a bottom opening of each disinfecting chamber with a portion to be disinfected exposed inside a chamber formed by the wall and the medial opening;
displacing the disinfecting members from the closed position to the open position to expose the disinfected portion of the medical implement; and
attaching a source of fluid to the medical implement.

The method may further include:
injecting the fluid into the medical implement;
detaching the source of fluid from the medical implement; and
displacing the disinfecting members from the open position to the closed position to bring the disinfecting members back in contact with the portion to be disinfected.

BRIEF DESCRIPTION OF THE DRAWINGS

The above and other aspects and features of the present disclosure will become more apparent by describing in detail exemplary embodiments thereof with reference to the attached drawings, in which:

FIG. 1 is a view of an embodiment of the capping device in a rest position, which is completely detached from a medical implement;

FIG. 2 is a cross-sectional view of an embodiment of the capping device, which is completely detached from a medical implement, and which shows a half of the disinfecting member at the top of a sealing member;

FIG. 3 is a cross-sectional view of an embodiment of the capping device, which is completely detached from a medical implement, and which shows a disinfecting member and an elevated rim of a sealing member;

DETAILED DESCRIPTION

Figure 4:
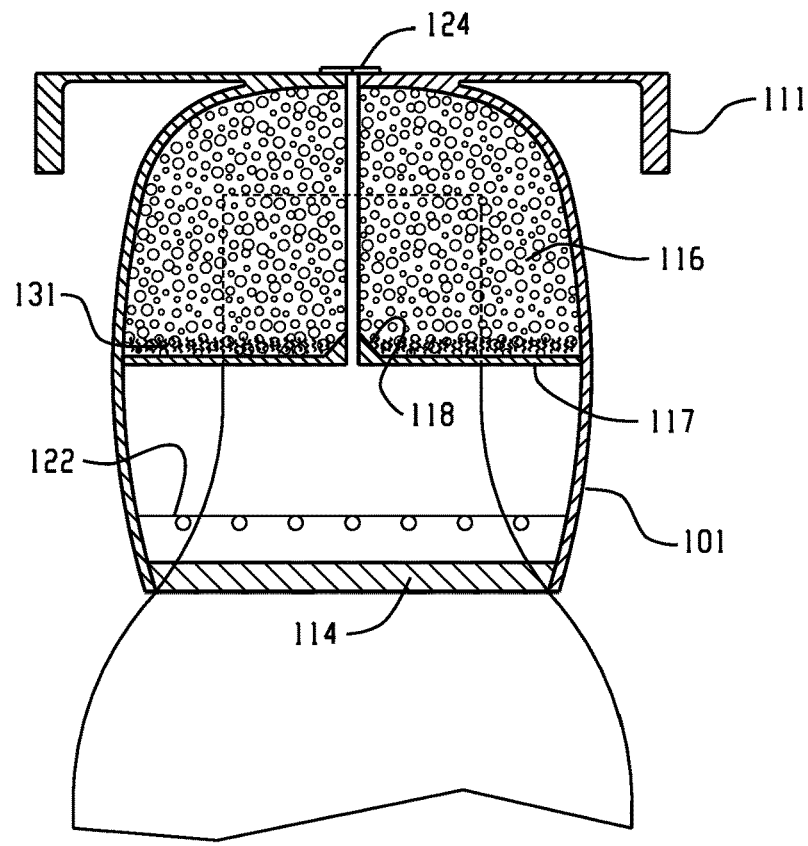
FIG. 4 is a cross-sectional view of an embodiment of the capping device in a rest position, which is attached to a medical implement.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below by referring to the figures to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross-section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"Substantially" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "substantially" can mean within one or more standard deviations, or within ±30%, 20%, 10%, 5% of the stated value.

In an embodiment, a device for disinfecting a portion of a medical implement is provided. The device includes two disinfecting chambers, wherein each disinfecting chamber includes a wall forming a medial opening and a bottom opening. The medial opening and the bottom opening are in communication with each other, and one disinfecting chamber is opposed to the other. Each disinfecting chamber houses a disinfecting member that is exposed through the medial opening to come into communication with a medical implement when the disinfecting chambers are closed. The device further includes a resilient member connected to the two disinfecting chambers, wherein the resilient member biases the disinfecting chambers together to a closed position and permits displacement of the disinfecting chambers to an open position, such that the medial opening of one disinfecting chamber communicates with the medial opening of the other disinfecting chamber and the bottom opening of one chamber communicates with the bottom opening of the other chamber when in the closed position. The medial and bottom openings of each disinfecting chamber are substantially configured to receive and be biased against a medical implement.

In another embodiment, the device further includes a medical implement protruded through a bottom opening of each disinfecting chamber with a portion to be disinfected exposed inside a chamber formed by the wall and the medial opening.

FIG. 1 depicts an embodiment of the capping device 100 in a rest position that is completely detached from a medical implement. The capping device and the medical implement may be permanently affixed to each other during manufacturing process so as to form a single entity. In another embodiment, the capping device and the medical implement may not be permanently affixed. This embodiment allows the disinfecting apparatus to be added to any medical implement on any intravenous line. An advantage of this embodiment is that the medical provider may choose to attach the disinfecting apparatus to a particular implement, which he or she frequently uses and not to all of them. The portion to be disinfected may be a needleless hub or an injection port. The medical implement may include a female luer fitting and an injection membrane.

The capping device 100 may include a pair of disinfecting chambers 112 opposing each other, which may be shaped to fully encircle the portion of the medical implement to be disinfected, where female luer threads and an injection membrane are located. Each disinfecting chamber includes a wall 101 forming a medial opening 102 and a bottom opening 115 that are in communication with each other. As shown in FIG. 2, each disinfecting chamber houses a disinfecting member 116 that is exposed through the medial opening to come into communication with a medical implement when the disinfecting chambers 112 are closed. The lateral movement of the two disinfecting chambers 112 causes the disinfecting members 116 to be displaced from a closed (rest) position to an open (engaged) position, in which the portion to be disinfected of the medical implement may be exposed to and accessed by a medical provider to make an injection.

The capping device 100 has a slit 113 which starts at the front of the device and extends over the top to the back of the device. In an embodiment, the slit 113 may substantially divide the capping device.

The capping device 100 may further include a resilient member 114 connected to the two disinfecting chambers, wherein the resilient member 114 biases the disinfecting chambers 112 together to a closed position and permits displacement of the disinfecting chambers 112 to an open position. As stated above, the capping device includes a bottom opening 115, through which a portion to be disinfected of medical implement enters the capping device. The bottom opening 115 may be covered by a protecting member, such as a peelable foil. The protecting member may provide a fluid barrier, which prevents loss of the disinfecting agent and drying of the disinfecting member before the capping device is used for the first time. The damaged peelable foil may indicate that the seal is broken. A medical professional would peel the foil immediately before connecting the apparatus with the implement.

The resilient member 114 also allows the capping device 100 to be attached to the medical implement. The bottom opening 115 has a diameter which is similar to the diameter of the neck of the most commonly used medical implements (such as hubs). The inner surface of the bottom opening 115 may be covered with an adhesive material. When the protective member is removed, the bottom opening 115 is revealed. The adhesive material may provide a better connection between the resilient member 114 and the neck of the medical implement. It also may also prevent leakage of the disinfecting agent when the sealing member fails to create a perfect seal. In an embodiment, the diameter of the bottom opening 115 of the disinfecting cap 100 matches the diameter of the access portion of the medical implement. Accordingly, the bottom opening of the disinfecting cap and the medical implement may be connected via a slip lock mechanism without the need for an adhesive.

Each of the disinfecting chambers may further include a side handle 111 or downward protrusions (not shown) to facilitate a lateral displacement of the disinfecting chambers. For easy gripping, the side handles 111 may include ridges disposed on their surface. The side handles 111 may be arranged such that a medical provider could open the device with a thumb and a forefinger of the same hand.

The disinfecting chambers may be made of a polyalkylene material (such as polyethylene or polypropylene), a polyester material, a polyurethane material, a silicone material, rubber, a cotton material, or a combination thereof. The resilient member must be made of a flexible, elastic material to enable movement of the disinfecting chambers to the engaged position when the external force is applied, and to ensure their subsequent return to the rest position.

FIG. 2 is a cross-sectional view of an embodiment of the capping device that is detached from a medical implement. The figure shows the disinfecting member 116 disposed in the upper portion of the disinfecting chamber 112. To minimize loss of the disinfecting agent, the disinfecting chamber 112 may further include a sealing member 117 that provides a seal with the portion of the medical implement to be disinfected. The sealing member divides the disinfecting chamber into an upper portion 103 containing a disinfecting member 116 and a hollow lower portion 104 containing the bottom opening 115. A central rim 118 of the sealing member 117 may be elevated to minimize the loss of the disinfecting agent.

FIG. 3 shows the disinfecting chamber 112 of the capping device 100 having a disinfecting member 116 and a sealing member 117 with an elevated rim 118. The disinfecting member 116 is located inside the upper portion of the disinfecting chamber 112. The disinfecting member 116 lines the interior of the disinfecting chamber and is affixed to its inner surface. In an embodiment, the disinfecting members 116 do not completely fill the entire disinfecting chambers 112 leaving a hollow, which matches the size and the shape of the medical implement portion to be disinfected. This compatibility guarantees that the disinfecting member is in close contact with the injection membrane and female luer threads of the medical implement. FIG. 3 also shows the side handle 111 attached to the disinfecting chamber 112. The figure further shows a top view of the medical implement having the injection membrane 119, the female luer threads 120, and a neck 121 to which the capping device 100 attaches. The design of a medical implement is well-known to a person of ordinary skill in the art, and will not be described here. For the purpose of this disclosure, only parts of the medical implement related to the present inventive concept are mentioned.

FIG. 4 shows a capping device attached to a medical implement in the rest position. In this position, the disinfecting members 116 may contact the medical implement and may further contact each other to completely cover the portion to be disinfected. In contrast, the portion to be disinfected may be completely uncovered in the engaged position. A disinfecting agent 131 may be disposed inside the reservoir chamber. The disinfecting members 116 may be impregnated (soaked) with the disinfecting agent. A small amount of the disinfecting agent 131 may be present near the sealing member 117 having an elevated rim 118. The figure also shows the resilient member 114 which substantially matches the diameter of the neck of the medical implement. In the rest position, the disinfecting chambers 112 may be connected by an optional click mechanism 124 which maintains the disinfecting chambers 112 closed, when the device is not in use. The capping device may further include an elastic band or a spring 122 connecting the disinfecting chambers 112 that returns the disinfecting chambers 112 to the rest position. In the rest position, the disinfecting members 116 may directly contact each other to completely cover the portion to be disinfected. In the engaged position, the portion to be disinfected may be completely uncovered. The disinfecting members 116 may have a substantial absorption capacity, so the pressure applied to an external surface of the walls of the disinfecting chambers 112 may cause compression of the disinfecting members 116 and release of the disinfecting agent 131 onto the injection membrane and around the female luer threads.

Figure 5:
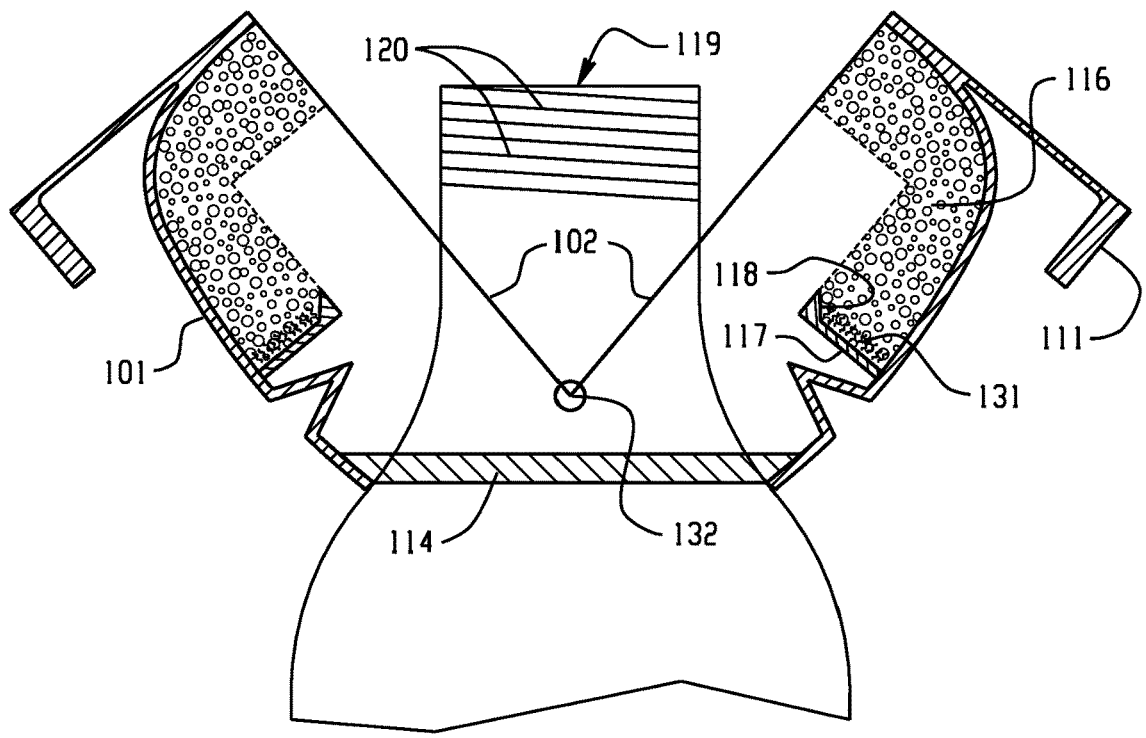
FIG. 5 is a cross-sectional view of an embodiment of the capping device in an engaged position, which is attached to a medical implement.

FIG. 5 shows the capping device in an open position. Application of pressure (force) on the side handles 111 permits displacement of the disinfecting members 116 in substantially opposite directions thereby creating a gap between the disinfecting chambers 112. As a result, the portion of the medical implement becomes accessible for an injection by the medical provider. The formed gap provides enough space for the syringe to enter inside the disinfecting cap to connect with the medical implement.

The complementary disinfecting members 116 are designed to completely cover the injection membrane in the rest position and completely encircle and come into intimate contact with the female luer threads of the medical implement. While the known prior art devices disinfect the injection membrane only, the capping device, according to an embodiment, completely and thoroughly disinfects both the injection membrane and the female luer threads. This arrangement ensures better disinfection results as the male luer threads on a syringe are often contaminated with bacteria or blood. After connection of the male luer threads from the syringe with the female luer threads from the medical implement, the blood or bacteria may remain on the female luer threads, and spread the contamination to the injection membrane. The present device completely prevents this from happening.

The capping device may include a click mechanism 124, an optional elastic band or spring 122, and a hinge mechanism 132, which increase the likelihood that a medical professional closes the capping device after operating it, and keeps the disinfected portion of the medical implement covered and in contact with the disinfecting agent. Having at least one of these optional devices, would guarantee 100% compliance of the medical professional.

Figure 6:
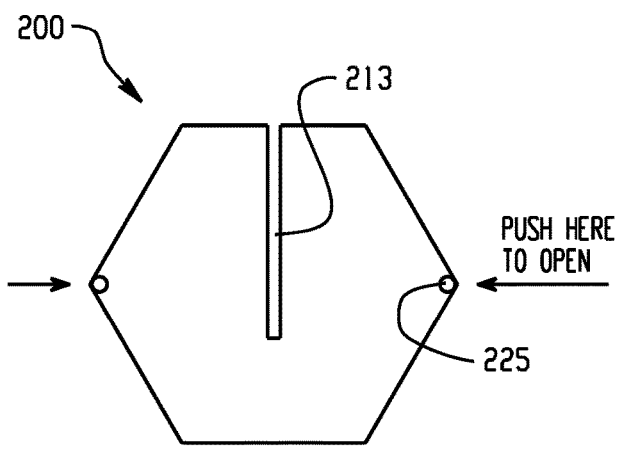
FIG. 6 is a view of another embodiment of the capping device in a rest position, which is completely detached from a medical implement.

FIG. 6 depicts another embodiment of a capping device 200 that is completely detached from a medical implement in the rest position. The device includes a slit 213 and an optional hinge mechanism 225 disposed on the wall of the disinfecting chamber, which would allow the medical provide to open the capping device by pressing on the hinge mechanism. In another embodiment, the wall of the disinfecting chamber may be made of a flexible material. In this embodiment, the medical professional would have to press on the external surface of the wall of the disinfecting chamber to open the capping device.

Figure 7:
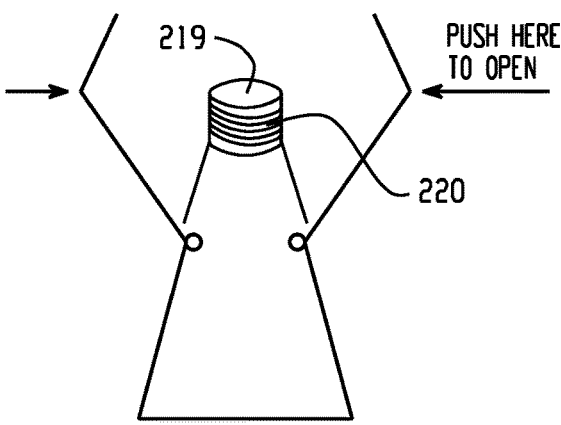
FIG. 7 is a view of another embodiment of the capping device in an engaged position, which is attached to a medical implement.

FIG. 7 is a schematic view of another embodiment attached to a medical implement. This embodiment shows an injection membrane 219 of the medical implement and female luer threads 220. The figure also shows the point of contact on the external surface of the wall that would allow a medical provider to bring the capping device to the engaged position.

Figure 8:
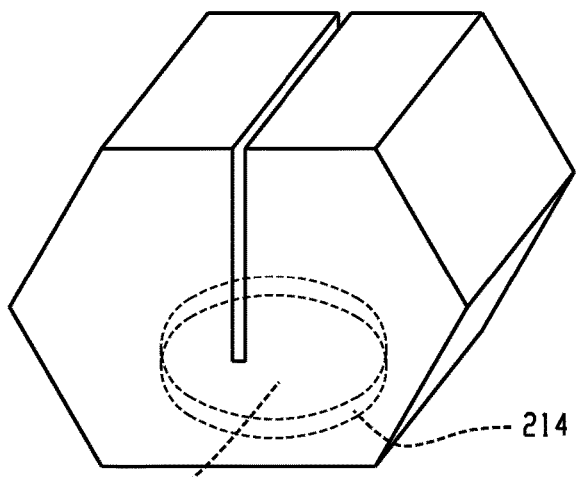
FIG. 8 is a perspective view of another embodiment of the capping device in a rest position, which is completely detached from a medical implement.

FIG. 8 depicts the capping device in the rest position that is completely detached from a medical implement. The dotted lines outline a bottom opening 215 where top of the medical implement enters as well as a resilient member 214.

Figure 9:
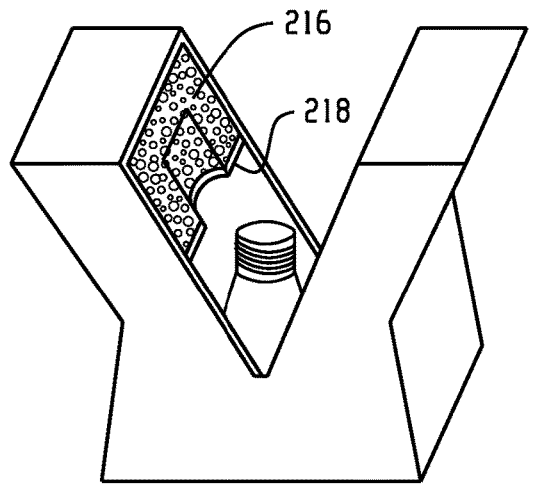
FIG. 9 is a perspective view of another embodiment of the capping device in an open position, which is attached to a medical implement.

FIG. 9 depicts the capping device attached to a medical implement in the open position. The device opens when the medical provider pushes near the middle of the walls on the external surface, causing the walls to move inside, and exposing the medical implement for connection with the syringe. The figure shows a disinfecting member 216 and an elevated rim 218 of the sealing member. The disinfecting member 216 is located inside the disinfecting chamber to line up the interior of the disinfecting chamber. The disinfecting member 216 is affixed to the inner surface of the disinfecting chamber. In this embodiment, the disinfecting member 216 does not completely fill the entire disinfecting chamber, leaving a hollow, which substantially matches the size and shape of the portion of the medical implement to be disinfected. This compatibility guarantees that the disinfecting members come into close contact with the injection membrane and female luer threads of the medical implement. The figure also shows a top view of the medical implement with its injection membrane, female luer threads and neck to which the medical implement attaches.

Figure 10:
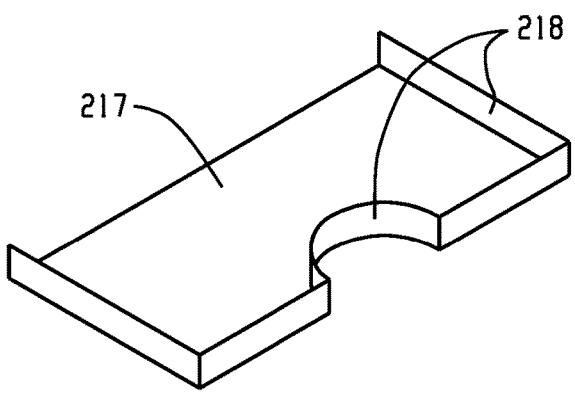
FIG. 10 is a view of a sealing member of the capping device according to an embodiment, wherein the sealing member has an elevated rim.

FIG. 10 shows one of two sealing members 217 with the elevated rim 218. The sealing member 217 provides a good seal with the access portion of the medical implement to minimize loss of the disinfecting agent. The elevated rim serves to minimize the loss of the disinfecting agent when the capping device is in the engaged position ready for connection with the syringe.

Figure 11:
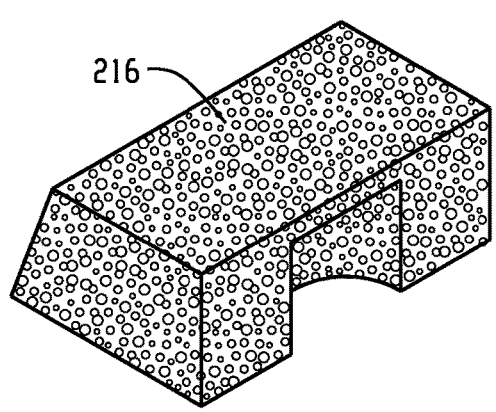
FIG. 11 is a view of one of the disinfecting members of the capping device according to an embodiment.

FIG. 11 shows an embodiment of the disinfecting member 216, which may be impregnated with the disinfecting agent. This embodiment has a hollow, which matches the size and shape of the access portion of the medical implement.

Figure 12:
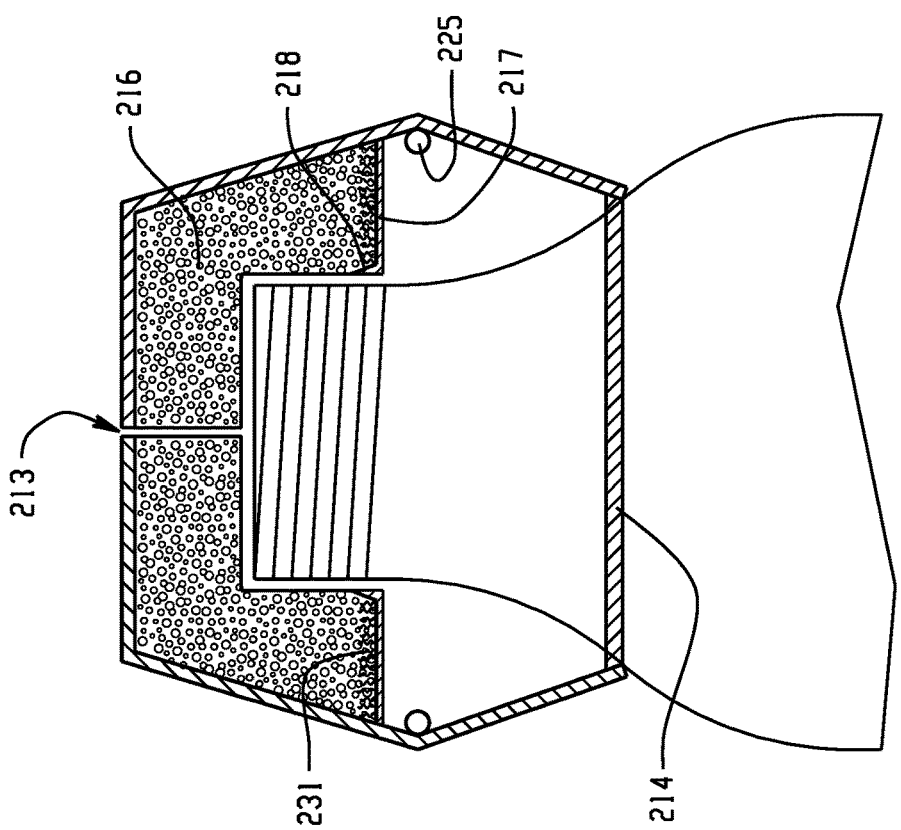
FIG. 12 is a cross-sectional view of another embodiment of the capping device in a rest position, which is attached to a medical implement.

FIG. 12 is a cross sectional view of an embodiment of the capping device attached to a medical implement in the rest position. The capping device includes a slit 213 and the disinfecting members 216 disposed around the medical implement. The disinfecting members 216 are located at the top of the sealing member 217 having an elevated rim 218. A small amount of a disinfecting agent 231 may be present at the top of sealing member 217 in the disinfecting chamber. A resilient member 214 is disposed around the neck of the medical implement. The disinfecting chambers may include an optional mechanism 225 used to place the device in the engaged position. The mechanism 225 may be biased to help return the capping device to the rest position after use, in which the disinfecting members 216 encircle the top of the medical implement.

Figure 13:
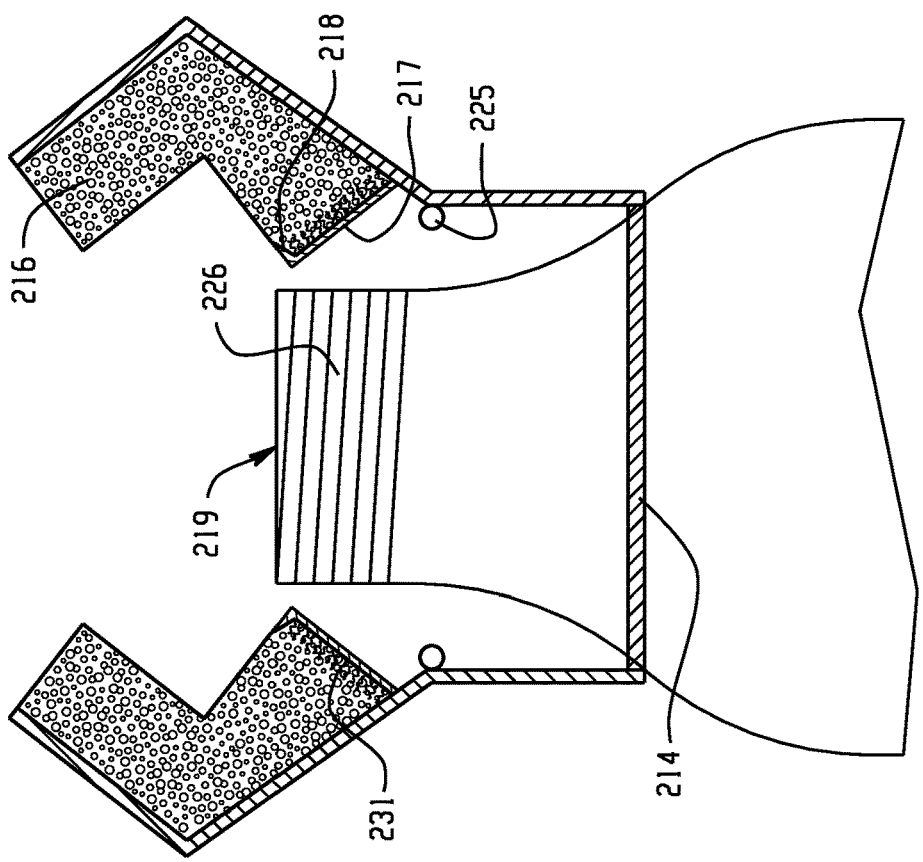
FIG. 13 is a cross-sectional view of another embodiment of the capping device in an engaged position, which is attached to a medical implement.

FIG. 13 shows the capping device in the engaged position, wherein an injection membrane 219 and female luer threads 226 are ready to connect with a syringe. When the optional mechanism 225 is not present, the opening and closing of the device takes place due to flexibility of the walls of the disinfecting chambers. The capping device may include a click mechanism, an optional elastic band or spring described above, which increase the chances that a medical professional would close the capping device after operating it, and would keep the portion of the medical implement to be disinfected covered and in contact with the disinfecting agent. Having at least one of these optional devices, would guarantee 100% compliance of the medical professional.

In another embodiment, a method for automatically disinfecting a portion of a medical implement is provided. The method includes providing a device for disinfecting a portion of a medical implement is provided. The device includes two disinfecting chambers, wherein each disinfecting chamber includes a wall forming a medial opening and a bottom opening. The medial opening and the bottom opening are in communication with each other, and one disinfecting chamber is opposed to the other. Each disinfecting chamber houses a disinfecting member that is exposed through the medial opening to come into communication with a medical implement when the disinfecting chambers are closed. The device further includes a resilient member connected to the two disinfecting chambers, wherein the resilient member biases the disinfecting chambers together to a closed position and permits displacement of the disinfecting chambers to an open position, such that the medial opening of one disinfecting chamber communicates with the medial opening of the other disinfecting chamber and the bottom opening of one chamber communicates with the bottom opening of the other chamber when in the closed position. The medial and bottom openings of each disinfecting chamber are substantially configured to receive and be biased against a medical implement. The device may further include a medical implement protruded through a bottom opening of each disinfecting chamber with a portion to be disinfected exposed inside a chamber formed by the wall and the medial opening.

The method may further include displacing the disinfecting members from the rest position to the engaged position to expose the disinfected portion of the medical implement and attaching a source of fluid to the medical implement.

The method may still further include injecting the fluid into the medical implement, detaching the source of fluid from the medical implement, and displacing the disinfecting members from the engaged position to the rest position to bring the disinfecting members back in contact with the portion to be disinfected.

The capping device, according to an embodiment of the present invention, provides a simple and affordable way to achieve perfect compliance of a medical professional with anti-septic techniques. Most of the known protective caps such as SwabCap® by ICU Medical or Curos® by 3M require both hands of the professional to attach or detach the cap from the medical implement. Once separated, the cap may be placed on a contaminated surface or even lost. The medical provider may then inadvertently place the contaminated cap onto the implement or may use a new cap to cover the implement.

By using the embodiments of the present invention, a medical provider can hold the medical implement in one hand and use the thumb and forefinger of the other hand to spread the side handles of the instant capping device apart exposing the portion to be disinfected of the medical implement for the injection. The provider may keep the side handles spread until the injection is complete. The provider may then use his or her other hand to hold a syringe and inject medication through the exposed hub. Once the injection is complete, the provider may slightly push the two disinfecting chambers medially (centrally, doing opposite of spreading handles) to close the device. If the optional click mechanism is present at the top of the device, the provider would assure they click into each other to stay together. When the optional band/string or optional hinge is used, the provider will only need to release the side handles so that the top covers would come together and shield the portion to be disinfected of the medical implement.

The present inventive concept has been described in terms of exemplary principles and embodiments, but those skilled in the art will recognize that variations may be made and equivalents substituted for what is described without departing from the scope and spirit of the disclosure as defined by the following claims.

What is claimed is:

1. A device for disinfecting a portion of a medical implement, wherein the portion to be disinfected comprises an injection membrane and female luer threads, the device comprising:
 a resilient member, and
 two disinfecting chambers connected to each other through the resilient member so as to form a continuous periphery defining a bottom opening having a predetermined size,
  wherein each disinfecting chamber comprises a wall and a medial opening, wherein the medial opening and the bottom opening are in communication with each other, and wherein one disinfecting chamber is opposed to the other, and
  wherein each disinfecting chamber houses a sealing member parallel to the bottom opening and a disinfecting member that is disposed on the sealing member, wherein each disinfecting member is exposed through its respective medial opening to come into communication with a medical implement when the two disinfecting chambers are closed, wherein the sealing member comprises an elevated central rim; and
  wherein the resilient member biases the two disinfecting chambers together to a closed position and permits displacement of the two disinfecting chambers to an open position,
  wherein, in the closed position, the disinfecting members fully enclose the portion to be disinfected so that each disinfecting member is in a direct and prolonged contact with the injection membrane and the female luer threads of the medical implement,
  wherein, in the open position, the disinfecting members are not contacting the medical implement or each other, and
  wherein the medial opening of each disinfecting chamber and the bottom opening are substantially configured to receive and be biased against the medical implement.

2. The device according to claim 1, wherein the sealing member of each disinfecting chamber is configured to separate the medial and bottom openings.

3. The device according to claim 1, wherein each disinfecting member is disposed over the entire surface of each disinfecting chamber.

4. The device according to claim 1, wherein the two disinfecting chambers further comprise a hollow internal space disposed between the disinfecting members and the medial openings, wherein the shape of the hollow internal space substantially matches the shape of the portion of the medical implement.

5. The device according to claim 1, wherein the two disinfecting chambers displace relative to each other so as to create a cavity between the two disinfecting chambers.

6. The device according to claim 1, wherein each disinfecting chamber further comprises a handle disposed on an external surface of the wall, and wherein the two disinfecting chambers displace by application of a force to the handles.

7. The device according to claim 1, wherein the two disinfecting chambers displace by application of a force directly to an external surface of each wall.

8. The device according to claim 1, wherein the disinfecting members directly contact each other in the closed position.

9. The device according to claim 1, wherein the disinfecting members are impregnated with a disinfecting agent.

10. A system for disinfecting a portion of a medical implement, wherein the portion to be disinfected comprises an injection membrane and female luer threads, the device comprising:
 a resilient member, and
 two disinfecting chambers connected to each other through the resilient member so as to form a continuous periphery defining a bottom opening having a predetermined size,
  wherein each disinfecting chamber comprises a wall and a medial opening, wherein the medial opening and the bottom opening are in communication with each other, and wherein one disinfecting chamber is opposed to the other, and
  wherein each disinfecting chamber houses a sealing member parallel to the bottom opening and a disinfecting member that is disposed on the sealing member, wherein each disinfecting member is exposed through its respective medial opening to come into communication with a medical implement when the two disinfecting chambers are closed, wherein the sealing member comprises an elevated central rim; and
  wherein the resilient member biases the two disinfecting chambers together to a closed position and permits displacement of the two disinfecting chambers to an open position,
 a medical implement protruded through the bottom opening of with the portion to be disinfected exposed inside the two disinfecting chambers,
  wherein, in the open position, the disinfecting members are not contacting the medical implement or each other,
  wherein, in the closed position, the disinfecting members fully enclose the portion to be disinfected so that each disinfecting member is in a direct and prolonged contact with the injection membrane and the female luer threads of the medical implement.

11. The system according to claim 10, wherein the disinfecting member of each disinfecting chamber is impregnated with a disinfecting agent, and wherein when the disinfecting member is in contact with the portion to be disinfected, the disinfecting member releases the disinfecting agent onto the portion to be disinfected.

12. The system according to claim 10, wherein the resilient member is permanently affixed to the medical implement so as to form a single entity.

13. The system according to claim 10, wherein the resilient member and the medical implement are not permanently affixed.

14. The system according to claim 10, wherein a combined internal surface of the walls of the two disinfecting chambers in the closed position fully encircles the portion of the medical implement to be disinfected.

15. The system according to claim 10, wherein the portion to be disinfected in the open position is completely uncovered.

16. A method for disinfecting a portion of a medical implement, comprising:
 providing the system according to claim 11;
 displacing the two disinfecting chambers from the closed position to the open position to expose the portion of the medical implement; and
 attaching a source of fluid to the medical implement.

17. The method according to claim 16, further comprising:
  injecting the fluid into the medical implement;
  detaching the source of fluid from the medical implement; and
  displacing the two disinfecting chambers from the open position to the closed position to bring the disinfecting members back in contact with the portion to be disinfected.

\* \* \* \* \*